(12) United States Patent
Barrientos

(10) Patent No.: US 7,608,085 B2
(45) Date of Patent: Oct. 27, 2009

(54) CATHETER HAVING END INCLUDING GROOVED NEEDLE GUIDES

(75) Inventor: Joel Kwan Barrientos, 58 Sherwood Dr., Centralia, IL (US) 62801

(73) Assignee: Joel Kwan Barrientos, Centralia, IL (US)

( * ) Notice: Subject to any disclaimer, the term of this patent is extended or adjusted under 35 U.S.C. 154(b) by 486 days.

(21) Appl. No.: 11/435,374

(22) Filed: May 16, 2006

(65) Prior Publication Data

US 2007/0270888 A1 Nov. 22, 2007

(51) Int. Cl.
*A61B 17/04* (2006.01)
(52) U.S. Cl. ...................... 606/148; 606/144
(58) Field of Classification Search ......... 606/144–150, 606/213, 198
See application file for complete search history.

(56) References Cited

U.S. PATENT DOCUMENTS

| 4,307,723 | A |   | 12/1981 | Finney | 128/349 |
| 4,553,543 | A | * | 11/1985 | Amarasinghe | 606/148 |
| 4,911,164 | A | * | 3/1990 | Roth | 606/148 |
| 5,480,407 | A | * | 1/1996 | Wan et al. | 606/148 |
| 5,496,332 | A | * | 3/1996 | Sierra et al. | 606/139 |
| 5,762,631 | A | * | 6/1998 | Klein | 604/171 |
| 2002/0188276 | A1 | * | 12/2002 | Evans et al. | 604/509 |
| 2005/0283193 | A1 | * | 12/2005 | Tullberg et al. | 606/232 |
| 2007/0276433 | A1 | * | 11/2007 | Huss | 606/213 |

* cited by examiner

*Primary Examiner*—(Jackie) Tan-Uyen T. Ho
*Assistant Examiner*—Melanie Tyson
(74) *Attorney, Agent, or Firm*—Harness, Dickey & Pierce, P.L.C.

(57) ABSTRACT

A catheter for use in suturing conduit shaped tissue within a subjects body, which includes a flexible tubular member having a proximal end portion, a distal end portion, and a lumen therebetween. The catheter includes a grooved tip member disposed on the distal end portion having a plurality of longitudinally extending grooves therein. The grooved tip member is configured to be positioned within adjoining portions of tissue to be sutured, such that a suture needle tip may be received within and guided by one of the plurality of grooves, to enhance suturing of adjoining tissue portions within a subject's body.

19 Claims, 2 Drawing Sheets

CATHETER HAVING END INCLUDING GROOVED NEEDLE GUIDES

FIELD

The present disclosure relates to catheters for use in radical prostatectomy surgical procedures, and more particularly to the procedure of anastomosis for joining two tubular body parts.

BACKGROUND

The statements in this section merely provide background information related to the present disclosure and may not constitute prior art. Surgical procedures generally referred to as a radical prostatectomy may require the removal of the entire prostate gland, after which a portion of the bladder and the urethra are attached through anastomosis. Anastomosis is the joining together of two tubular body conduits that are generally cylindrical and have a circular cross-section. Such conduits may be joined by inserting sutures around the circumference of the body conduits. A suture insertion though the conduit from the outside may be made more easily relative to sutures inserted through the conduit from the inside of the conduit, where the suture is not readily visible. The suturing together of the bladder and urethra is also typically done while a catheter is inserted and positioned within the body conduit portions, which adds to the difficulty and complexity of making the sutures.

SUMMARY

Embodiments of the present invention provide for a catheter and catheter tip for use in performing radical prostatectomy procedures. The various embodiments are useful for robot assisted Radical Prostatectomy, but should not exclude use for other surgeries. In accordance with certain embodiments, a catheter for use in suturing conduit shaped tissue within a subjects body is provided that includes a flexible tubular member having a proximal end portion, a distal end portion, and a lumen therebetween. The catheter includes a grooved tip member disposed on the distal end portion having a plurality of longitudinally extending grooves therein. The grooved tip member is configured to be positioned within adjoining portions of tissue to be sutured, such that a suture needle tip may be received within and guided by one of the plurality of grooves, to enhance suturing of adjoining tissue portions within a subject's body.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
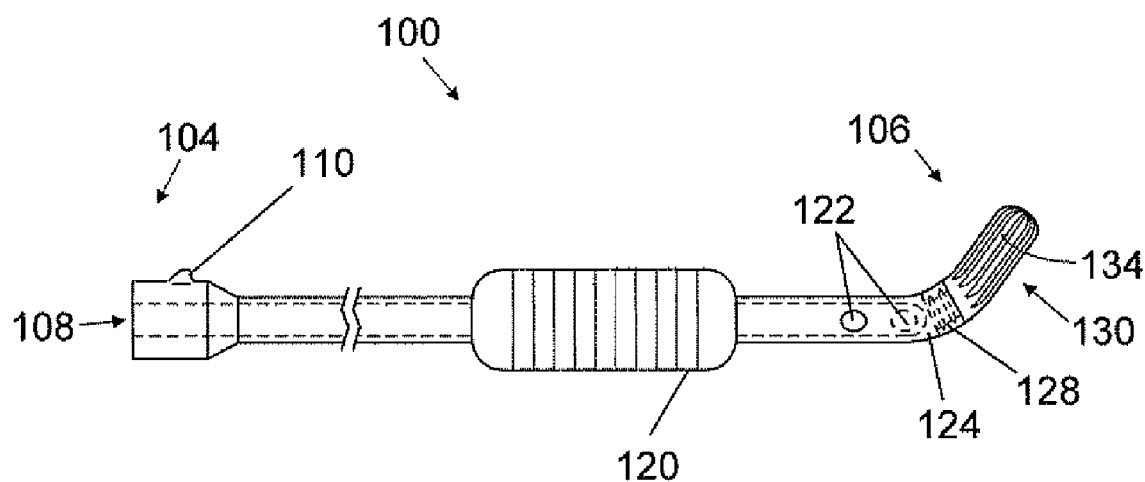
FIG. 1 is a side elevation view of one embodiment of a catheter having a curved end with a plurality of groves therein.

The following description is merely exemplary in nature and is not intended to limit the present disclosure, application, or uses. The structure of a catheter and catheter tip for use in radical prostatectomy procedures in accordance with the present disclosure is now described in greater detail. The following description of the illustrated example is merely exemplary in nature and is in no way intended to limit the invention, its application, or uses. It should be understood that throughout the drawings, corresponding reference numerals indicate like or corresponding parts and features.

Referring to FIG. 1, one embodiment of a catheter in accordance with the teachings of the present disclosure is illustrated and generally indicated by reference numeral 100. The catheter 100 comprises a flexible tubular member 102 having a proximal end 104, a distal end portion 106, and a lumen 108 therebetween. The distal end portion 106 of the catheter includes an expandable member 120 that may be inflated or deployed to operatively anchor or secure the distal end of the catheter 100 in place within one or more body conduits that are to be sutured, such as in performing radical prostatectomy procedures. The proximal end of the catheter 100 preferably includes a balloon inflation port, for inflating the expandable member 120. Such catheters may be used with robot-assisted radical prostatectomy, and also for laparoscopic radical prostatectomy. The distal end portion 106 of the catheter 100 further includes one or more drain holes 122 in the distal end portion 106, which are positioned on opposing sides of the catheter in a staggered arrangement. The drain holes 122 are preferably staggered to maintain catheter rigidity and consistency in the flexibility of the catheter, but may alternatively be positioned at the distal end portion 106 in any desirable manner. The drain holes 122 are functional to allow for drainage of fluid through the lumen 108. The catheter 100 made be made of a flexible material such as Latex, silicon or any material suitable for indwelling use within a subject's body. The flexibility of the catheter 100 allows the catheter to be easily advanced within a subject to the bladder, and minimize the trauma risk associated with the use of a hard or rigid-shaft type catheter instrument. The flexibility of the catheter 100 also allows the catheter to be left within the patient for indwelling purposes, unlike a hard or rigid-shaft type catheter instrument.

Figure 2:
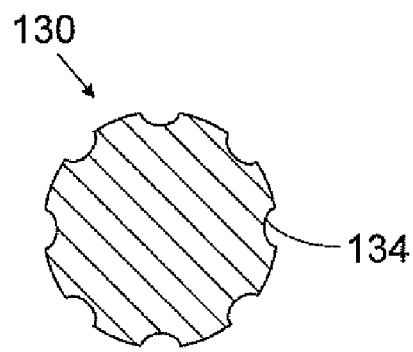
FIG. 2 is a cross-sectional view of the end of the first embodiment of a catheter.
Figure 4:
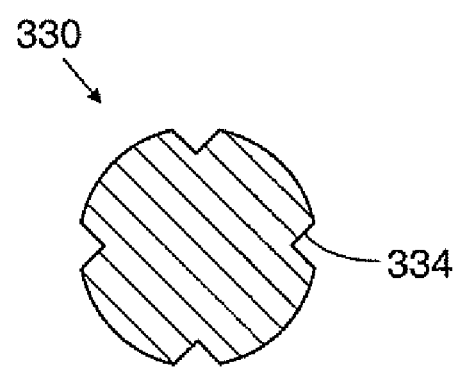
FIG. 4 is a cross-sectional view of the end yet another embodiment of a catheter, in accordance with the principles of the present invention.

The catheter 100 may be a styled catheter, in which the distal end portion 106 of the catheter 100 has a curved solid end portion 124. The catheter 100 also includes a knob 110 that is positioned at the proximal end 102 for aligning the curved solid end portion 124. As shown in FIG. 1, the knob 110 is aligned with the curve shape in the distal end portion. The curved solid end portion 124 is configured to attachably receive a grooved tip member 130. The curved solid end portion 124 includes an internal opening 126 therein, having one or more annular grooves 128 in which an end of the grooved tip member 130 is received. It should be noted that the annular grooves 128 may alternatively comprise internal threads or other suitable means for attaching or securing the grooved tip member 130 to the end of the catheter. As shown in FIG. 2, the grooved tip member 130 includes a number of grooves 134 thereon, which may be in the range of eight grooves 134, but may alternatively be in the range of four grooves (as shown in FIG. 4).

The grooved tip member 130 has a diameter that is generally consistent with the diameter of the catheter. The grooved tip member 130 has a plurality of grooves 134 extending longitudinally along the outer surface 136 of the tip member 130, which are spaced apart in a radical arrangement around the diameter of the tip member 130. The plurality of grooves 134 will facilitate the suture needle placement in the anastomosis of a body conduit tissue, such as the urethral stump to the bladder neck, for example. The tip member 130 also prevents or resists accidental puncturing of the catheter balloon 120 by the suture needle, or accidental catching of the opposite wall in the urethra by the suture needle. In the embodiment shown in FIG. 1, the grooved tip member 130 includes a slightly curved shape. Likewise, the plurality of grooves 134 in the tip member 130 may also be slightly curved. The first embodiment of a catheter 100 preferably has eight grooves 134 arranged around the diameter of the tip member 130, with a radical spacing of about 45 degrees between each groove 134. Each groove has a length in the range of about 10 to 20 millimeter (about 0.4 to 0.8 inches), and a depth of about 0.50 to 1.5 millimeter (about 0.020 to 0.060 inches). The grooves may have a width in the range of about 0.5 to 2.0 millimeter (about 0.020 to 0.080 inches). More preferably, each groove has a length of about 15 millimeter (about 0.6 inches), and a depth of about 1.0 millimeter (about 0.040 inches). Each of the plurality of grooves 134 extend to the end, or near the end, of the tip member 130. The length of the grooved tip member 130 is preferably in the range of about 15 to 20 millimeter (about 0.6 to 0.75 inches). The grooved tip member 130 is preferably made of hard plastic or ceramic material suitable for orthopedic use. The material for the tip member 130 preferably comprises the characteristics of a non-porous material, a non-conductive material, a non-reactive material, and a corrosion-resistant material. The tip member may alternatively be made of stainless steels suitable for use in surgical procedures, where there may be a concern of a possible corrosive issue in an acid environment such as in urine in the bladder. Where a stainless steel material is used, the surface may have a matte finish to avoid the potential for glare in operating procedures. The tip member 130 is attached to the solid end portion 124 of the catheter 100, and is preferably permanently vulcanized to the end 124 of the catheter. The grooved tip member may also comprise a latex cover over at least a portion thereof, but preferably has a length of about 15 to 20 millimeter (about 0.6 to 0.75 inches) that is exposed and not covered by the latex.

Referring to a cross-section of the tip member 130 shown in FIG. 2, the grooves 134 act as guides for guiding a needle during suturing of adjoining body conduit portions. The grooves 134 preferably have a generally curved cross-section, but may alternatively comprise rectangular or triangular cross-sections as well. Once a suture needle has been inserted though the body conduit, the tip of the needle is preferably located within one of the grooves 134 in the tip portion 130. After the suture needle is inserted through the conduit, the needle tip may then be advanced and follow the groove track before the needle exits through the body conduit tissue in the adjoining portion. The plurality of grooves 134 positioned around the tip member 130 allow for accurate guidance and placement of sutures around the circumference of the tissue conduit.

In the various embodiments, the catheter has sufficient flexibility to allow the catheter to be easily advanced within a subject to the bladder, to minimize the trauma risk associated with the use of a hard or rigid-shaft type catheter instrument. The flexibility of the catheter 100 also allows the catheter to be left within the patient for indwelling purposes, unlike a hard or rigid-shaft type catheter instrument. In the various embodiments, the catheter is also a fully functioning Foley-type catheter with urine drain holes 122, and an expandable member or balloon 120 for indwelling use after the urethra-bladder neck anastomosis is completed. The proximal end of the catheter is preferably connectable to a Foley type tube or bag for delivery of urine. This feature cuts the number of catheters used during both intra-operatively and post anastomosis of urethra to bladder neck to only one catheter, rather than removing an intra-operative catheter and a second post-operative catheter. This minimizes the risk of traumatic disruption of the anastomotic suture line, since the present catheter serves as a fully functional Foley-type catheter and is already in place after the operative procedure.

Figure 3:
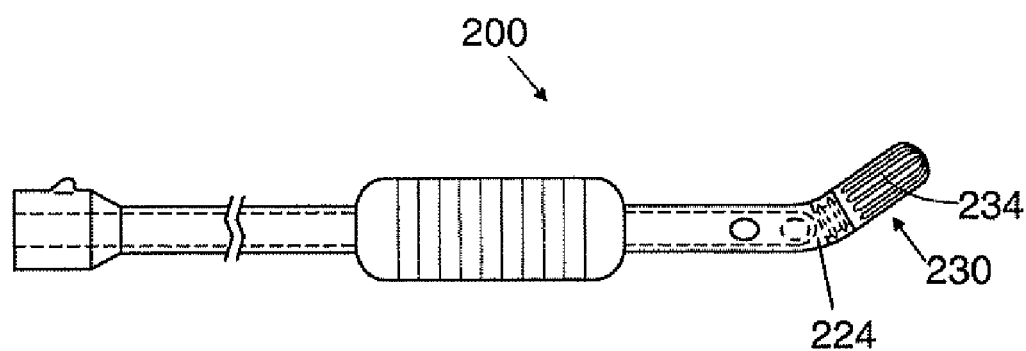
FIG. 3 is a side elevation view of another embodiment of a catheter having a coude shaped end with a plurality of groves therein.

In the various embodiments, the catheter's distal end portion may comprise any number of curved shapes, and may include a Coude type curved tip. The grooved tip member 130 may form an angle in the range of 90 to 120 degrees relative to the longitudinal axis of the catheter length. Referring to FIG. 3, a catheter 200 similar to that in FIG. 1 is shown that has a curved solid end portion 224, which is configured to attachably receive a grooved tip member 230. The curved solid end portion 224 includes an internal opening 226 therein, having one or more grooves 228 in which an end of the grooved tip member 230 is received. The grooved tip member 230 in the second embodiment comprises a generally straight configuration, and includes a plurality of longitudinal grooves 234 therein. The grooves 234 are similar in size and shape to the first embodiment, but have a generally straight configuration corresponding to the straight configuration of the tip member 230.

Referring to the cross-section of a tip member shown in FIG. 4, another embodiment of a catheter is shown that comprises only four grooves 334 positioned around the diameter of a tip member 330. The grooves 334 preferably have a notched or triangular cross-section, and are arranged around the diameter of the tip member 330, with a radical spacing of about 90 degrees between each groove 334. The notched grooves 334 also act as guides for guiding a needle during suturing, and allow for accurate guidance and placement of sutures around the circumference of the tissue conduit.

It should be noted that the above embodiments may include variations the curved shape of the distal end portion, the diameter of the catheter, the number of grooves in the distal tip member, and the dimensions in the length, depth and width of the individual grooves. For example, various embodiments of the catheter according to the principles of the present invention may be a French size 14, 16, 18, 20, 22, and 24, which have an outside diameter of about 5.3, 5.7, 6.0, 6.3, 6.7, 7.3 and 8.0 millimeter respectively. The cross-section of the grooves may also be deeper or wider in dimension, to accommodate different size suture needles. Likewise, the number of grooves may be a few as four, to as many as may reasonably be positioned on the tip member of the catheter. Without departing from the spirit and scope of the above concepts, other similar methods and implementations can be derived from the teachings described herein by persons skilled in the art of remote navigation. The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A single catheter for use in suturing conduit shaped tissue within a subjects body, the catheter comprising:

a flexible catheter having a proximal end portion configured to be connected to a urine collection bag, a distal end portion, and a lumen therebetween, the flexible catheter including:

one or more drain holes disposed in the distal end portion of the catheter, and an inflatable expandable balloon attached to the flexible catheter at a location proximally spaced from the one or more drain holes disposed in the distal end portion, the inflatable expandable balloon being configured to be expanded within the conduit shaped tissue to anchor the catheter for indwelling purposes;

a grooved tip member disposed on the distal end portion of the flexible catheter, having a plurality of longitudinally extending grooves on an external surface of the tip member, the grooved tip member being configured to be positioned within adjoining portions of tissue to be sutured, such that a suture needle tip may be received within and guided by one of said plurality of grooves during suturing of adjoining tissue portions within a subject's body; wherein the one or more drain holes disposed in the distal end of the catheter are located between the grooved tip member and the inflatable expandable balloon to provide for drainage of urine through the lumen to the proximal end portion of the catheter, and the catheter is made of a material with a flexibility sufficient to enable the catheter to be left within the patient for indwelling purposes after suturing to provide for drainage of urine.

2. The catheter of claim 1 wherein the grooved tip member is generally straight in configuration.

3. The catheter of claim 2 wherein the plurality of grooves are generally straight in configuration.

4. The catheter of claim 1 wherein the grooved tip member is slightly curved in shape.

5. The catheter of claim 4 wherein the plurality of grooves are slightly curved in shape corresponding to the curved shape of the tip member.

6. The catheter of claim 5 further including a knob at the proximal end portion that is positioned in alignment with a curve shape in the distal end portion.

7. The catheter of claim 6 wherein the one or more drain holes are positioned on opposing sides of the catheter and staggered to maintain consistency in the flexibility of the catheter.

8. The catheter of claim 6 wherein the plurality of grooves is in the range of 4 or 8 grooves.

9. A single catheter for use during an anastomosis procedure in suturing conduit shaped tissue within a subjects body, the catheter comprising:

a flexible tubular member having a proximal end portion configured to be connected to a urine collection bag, a distal end portion, and a lumen therebetween; wherein the catheter is made of a flexible material comprising latex or silicone such that the flexibility of the catheter enables the catheter to be left within the patient for indwelling;

one or more drain holes disposed in the distal end portion of the flexible tubular member, and an inflatable expandable balloon member attached to the flexible tubular member at a location proximally spaced from the one or more drain holes disposed in the distal end portion of the flexible tubular member, the inflatable expandable balloon member being configured to be expanded to operatively anchor the distal end of the flexible tubular member in place within the conduit shaped tissue;

a grooved tip member disposed on the distal end portion, having a plurality of longitudinally extending grooves on an external surface of the tip member, the grooved tip member being configured to be positioned within adjoining portions of tissue to be sutured, such that a suture needle tip may be received within and guided by one of said plurality of grooves during suturing of adjoining tissue portions within a subject's body, wherein the one or more drain holes in the distal end portion of the flexible tubular member are located between the grooved tip member and the inflatable expandable balloon to provide for drainage of urine fluid flow through the lumen, such that the catheter having the grooved tip member and one or more drain holes is configured to be used during suturing of conduit shaped tissue and to remain in place after suturing to serve as a Foley-type catheter for drainage of urine, to thereby reduce the risk of trauma associated with conventional anastomosis procedures that require the removal of both an intra-operative catheter and a second post-operative catheter.

10. The catheter of claim 9 wherein the grooved tip member is generally straight in configuration.

11. The catheter of claim 10 wherein the plurality of grooves are generally straight in configuration.

12. The catheter of claim 9 wherein the grooved tip member is slightly curved in shape.

13. The catheter of claim 12 wherein the plurality of grooves are slightly curved in shape corresponding to the curved shape of the tip member.

14. The catheter of claim 13 further including a knob at the proximal end portion that is positioned in alignment with a curve shape in the distal end portion.

15. The catheter of claim 14 wherein the tip member is made of one of a group consisting of ceramic, plastic or stainless steel.

16. The catheter of claim 14 wherein the plurality of grooves is in the range of 4 or 8 grooves.

17. The catheter of claim 16 wherein the plurality of grooves comprise a generally curved cross-sectional contour.

18. The catheter of claim 16 wherein the plurality of grooves comprise a generally triangularly notched cross-section.

19. The catheter of claim 17 wherein the flexible material permits the catheter to be guided through the body, and the grooved tip member comprise a generally rigid material to provide support and resist puncture by a suture needle during suture of adjoining portions of conduit tissue within a subject's body.

* * * * *

UNITED STATES PATENT AND TRADEMARK OFFICE
CERTIFICATE OF CORRECTION

PATENT NO.      : 7,608,085 B2                                      Page 1 of 1
APPLICATION NO. : 11/435374
DATED           : October 27, 2009
INVENTOR(S)     : Joel Kwan Barrientos It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 551 days.

Signed and Sealed this

Twelfth Day of October, 2010

David J. Kappos
*Director of the United States Patent and Trademark Office*